United States Patent
Siljkovic (10) Patent No.: US 11,219,554 B2
(45) Date of Patent: Jan. 11, 2022

(54) EAR CLEANING DEVICE

(71) Applicant: Hamlet Siljkovic, Pottsville, PA (US)

(72) Inventor: Hamlet Siljkovic, Pottsville, PA (US)

( * ) Notice: Subject to any disclaimer, the term of this patent is extended or adjusted under 35 U.S.C. 154(b) by 55 days.

(21) Appl. No.: 16/651,162

(22) PCT Filed: Mar. 15, 2018

(86) PCT No.: PCT/US2018/022736
§ 371 (c)(1),
(2) Date: Mar. 26, 2020

(87) PCT Pub. No.: WO2019/099056
PCT Pub. Date: May 23, 2019

(65) Prior Publication Data
US 2020/0268556 A1    Aug. 27, 2020

Related U.S. Application Data

(60) Provisional application No. 62/586,562, filed on Nov. 15, 2017.

(51) Int. Cl.
*A61F 11/00*    (2006.01)

(52) U.S. Cl.
CPC .................................. *A61F 11/006* (2013.01)

(58) Field of Classification Search
CPC ......... A61F 13/38; A61F 13/12; A61F 11/006
See application file for complete search history.

(56) References Cited

U.S. PATENT DOCUMENTS

| | | | |
|---|---|---|---|
| 6,187,021 B1* | 2/2001 | Wim | A61F 11/006 606/161 |
| 6,695,802 B1* | 2/2004 | Thompson | A61F 11/006 604/1 |
| 2003/0187469 A1* | 10/2003 | Olson | A61F 11/006 606/162 |
| 2005/0267395 A1 | 12/2005 | Mangold et al. | |
| 2006/0085018 A1* | 4/2006 | Clevenger | A61F 11/006 606/162 |
| 2006/0190020 A1* | 8/2006 | Eicoff | A61F 11/006 606/162 |
| 2007/0299457 A1 | 12/2007 | Morales | |
| 2015/0018861 A1 | 1/2015 | Olson | |
| 2015/0351968 A1* | 12/2015 | Shane | A61F 11/006 606/162 |
| 2016/0361203 A1 | 12/2016 | Khademhosseini | |

OTHER PUBLICATIONS

International Search Report, International Application No. PCT/US2018/022736, dated May 23, 2018.
Written Opinion of the ISA, International Application No. PCT/US2018/022736, dated May 23, 2018.

* cited by examiner

*Primary Examiner* — Jocelin C Tanner
(74) *Attorney, Agent, or Firm* — Law Office of David Zivan, P.C.

(57) ABSTRACT

An ear cleaning device (100) including a rod (102) configured to be held by a user and a plurality of fiber hooks (110) is disclosed. The rod includes a first end (104) and a second end (106) opposing the first end. The plurality of fiber hooks are disposed at the first end of the rod for insertion into the ear such that the fiber hooks are configured to grasp ear wax in the ear, and to hold the ear wax when the rod is removed out of the ear.

15 Claims, 7 Drawing Sheets

EAR CLEANING DEVICE

RELATED APPLICATION INFORMATION

This application is the U.S. National Phase application under 35 U.S.C. § 371 of International Application No. PCT/US2018/022736, filed on Mar. 15, 2018 and incorporated herein by reference, which claims priority to U.S. Provisional Application Ser. No. 62/586,562, filed on Nov. 15, 2017 and incorporated herein by reference.

TECHNICAL FIELD

The present invention is directed to cleaning apparatus and devices, and more particularly to apparatus and devices for cleaning ear wax out of ears.

BACKGROUND

For the past several decades, cotton swabs, composed of a rod and a cotton bulb at ends of the rod, have been a common means employed by the general public to clean out ear wax. However, medical professionals advise against the use of cotton swabs, as it may result in pushing ear wax farther into the ear canal and/or puncturing the ear drum. Alternative cleaning devices employ bulbs with a scoop, as discussed in U.S. Patent Application Publication No. 2003/0187469, or a plurality of pockets, as described in U.S. Patent Application Publication No. 2015/0018861.

SUMMARY

While the above-referenced ear cleaning devices employ cavities for purposes of aiding the collection of ear wax, or cerumen, a problem with these devices is that their use may nonetheless push ear wax farther into the ear canal, thereby causing a reduction in sound perception or even perforation of the ear drum. Exemplary embodiments of the present invention can reduce the incidence of pushing ear wax into the ear canal, while at the same time significantly improve grasping and removal of ear wax from the ear.

One exemplary embodiment is directed to an ear cleaning device including a rod configured to be held by a user, wherein the rod includes a first end and a second end opposing the first end. The device further includes a plurality of fiber hooks disposed at the first end of the rod for insertion into the ear such that the fiber hooks are configured to grasp ear wax that is in the ear, and to hold the ear wax when the rod is removed out of the ear.

BRIEF DESCRIPTION OF THE DRAWINGS

The advantages, nature, and various additional features of exemplary embodiments of the present invention described herein will appear more fully upon consideration of the illustrative embodiments now to be described in detail in connection with accompanying drawings. In the drawings wherein like reference numerals denote like components throughout the views.

DETAILED DESCRIPTION OF PREFERRED EMBODIMENTS

The present principles are directed to ear cleaning devices and apparatus. Current devices employed for cleaning ear wax, including cotton swabs and other devices, pose a risk of pushing ear wax into the ear canal, which can cause reduction in sound perception or perforation of the ear drum. Exemplary embodiments of the present invention can provide an efficient means of removing ear wax, also referred to as cerumen, while at the same time reducing the risk of pushing ear wax into the ear canal. For example, in accordance with one exemplary aspect, hook fibers, which can have the same or similar structure as hooks in hook and loop fasteners, can be employed at the end of a rod of an ear cleaning device. Here, the hooks are structured and oriented to slide over ear wax disposed on the wall of the ear canal as the device is inserted into an ear canal, thereby reducing the extent to which the ear wax is pushed farther into the ear or avoiding pushing the ear wax farther into the ear entirely. For example, the hooks can be oriented so that the hook opening faces towards the opposing end of the rod. Accordingly, the hook fibers can grip the ear wax as the device is pulled out of the ear canal, thereby facilitating the removal of the ear wax from the ear.

Figure 1:
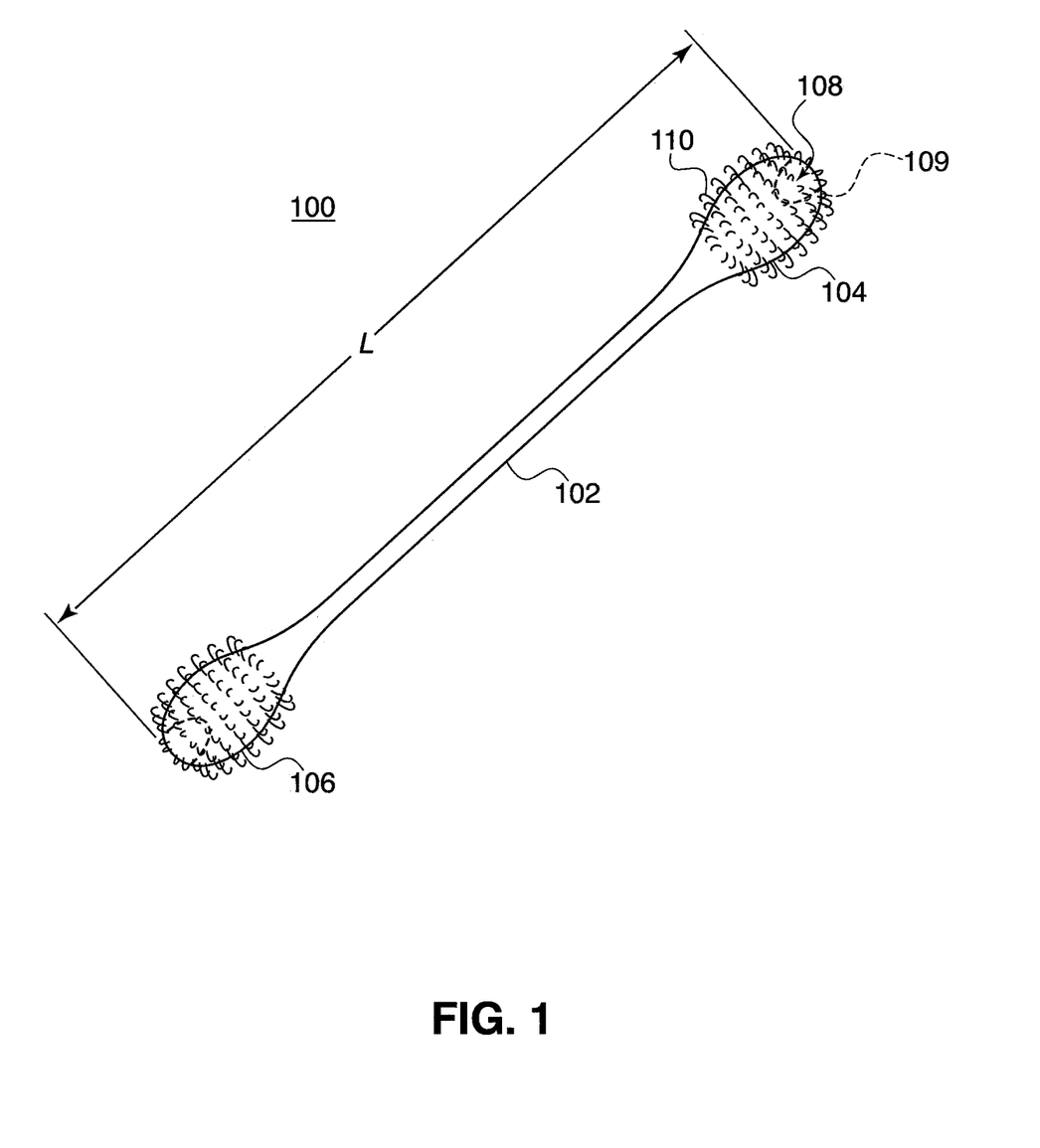
FIG. 1 is a drawing of an ear cleaning device of an exemplary embodiment of the present application.

With reference now to FIG. 1, an ear cleaning device 100 in accordance with an exemplary embodiment is illustratively depicted. The ear cleaning device 100 includes a rod 102, a first end 104 and a second end 106 that opposes the first end 104. Here, the first end 104 and the second end 106 can have the same structure. The rod 102 can be composed of rolled paper, plastic, wood or any other suitable material. The ends 104 and 106 can have a bulbous configuration, as illustrated in FIG. 1, and can be formed of the same material as the rod portion 102 or a different material. For example, the end portions 104, 106 can be composed of foam attached to the rod 102 by an adhesive or the end portions 104, 106 can be composed of a hard plastic. In addition, the ear cleaning device includes hook fibers 110. It should be noted that the hook fiber sizes and their density in an area of the end portions are not to scale and have been altered for ease of understanding. As shown in FIG. 1, at least a majority of fiber hooks 110, preferably all of the hooks 110, on end portions 104, 106 are concave with respect to an axis of the rod. For example, the rod 102 may be essentially cylindrical and have a central axis 402 as illustrated in FIG. 4. Here, from the view point of the rod 102, or, in other words, with respect to the rod, at least a majority of fiber hooks 110, preferably all of the hooks 110, on end portions 104, 106 are concave. In other words, the openings 316, as opposed to the back 318 illustrated in FIG. 3, of the hooks of at least a majority of fiber hooks 110, preferably all of the hooks 110, on end portions 104, 106 face towards the rod 102, as illustrated, for example, in FIGS. 1, 2, 5-8, 13 and 14. In addition, at least a majority of fiber hooks 110, preferably all of the hooks 110, are oriented, in accordance with a preferred embodiment, parallel to the central axis 402.

Figure 2:
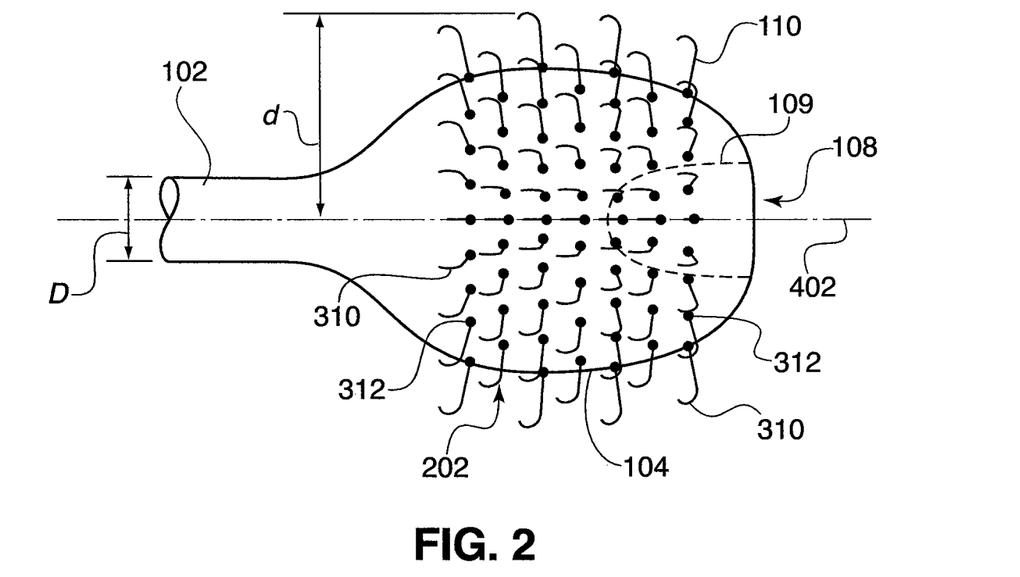
FIG. 2 is a drawing of an end of an ear cleaning device of an exemplary embodiment of the present application.
Figure 3:
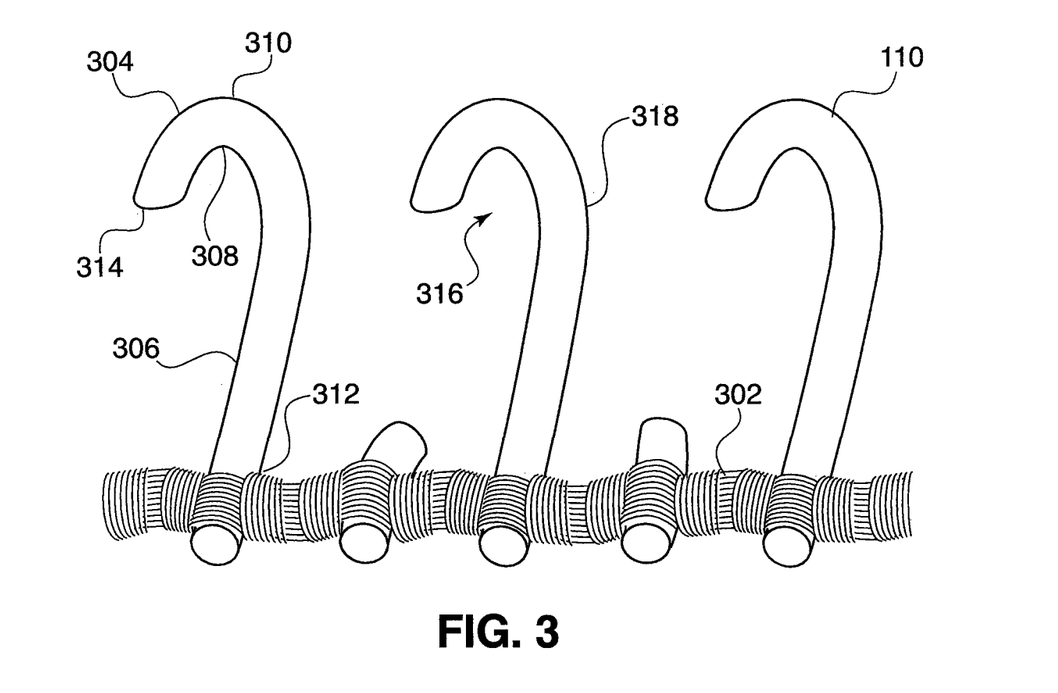
FIG. 3 is a drawing of hooks disposed at an end of an ear cleaning device in accordance with an exemplary embodiment of the present application.
Figure 4:
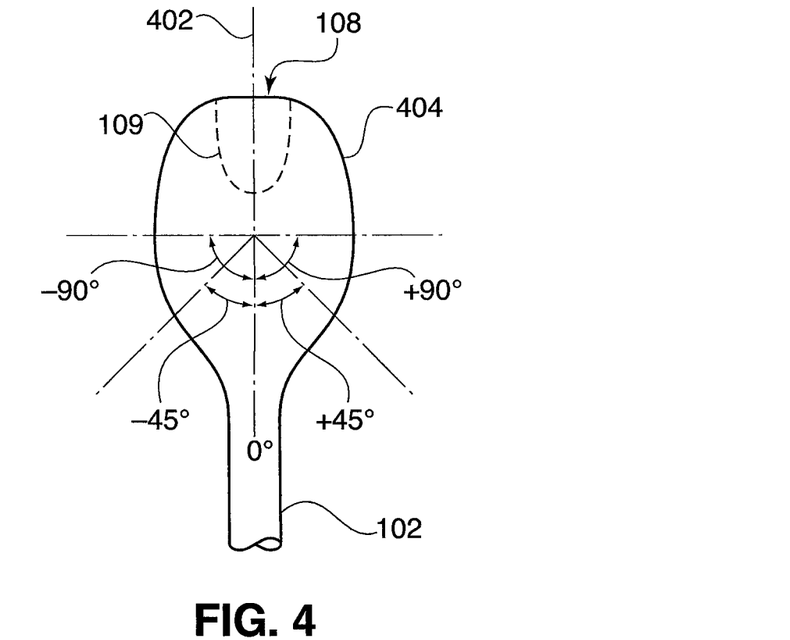
FIG. 4 is a drawing of an end of an ear cleaning device of an exemplary embodiment that provides a reference coordinate system employed to describe the angular orientation of hooks in accordance with various exemplary embodiments of the present application described herein.

For example, referring to FIGS. 2-4, with continuing reference to FIG. 1, a top view of an end portion 104 is illustrated in FIG. 2, while a top view of an end portion 404, which can be end portion 104 and/or 106, is illustrated in FIG. 4. FIG. 3 depicts a magnified view of the hooks 110. As shown in FIG. 3, the hooks are structured in the same way as hooks in hook and loop fasteners. Here, the hooks 110 are woven into a base 302, as shown in FIG. 3, and can be composed of nylon. However, it should be understood that any material suitable for removing ear wax as discussed herein can be employed as the hook 110 material. The hooks 110 include a stem 306 and a curved portion 304. In addition, the hooks can be attached to a bulbous portion at an end 104 and/or 106 of the rod 102 by applying an adhesive, for example an epoxy adhesive and/or any other suitable glue, to the base portion 302 and attaching the base portion to the bulbous portion at an end 104 and/or 106 of the rod 102. Alternatively or additionally, the hooks 110 can be attached to the bulbous portion at an end 104 and/or 106 of the rod 102 directly with this adhesive without the base portion 302. The hooks 110 in FIG. 2 are oriented so that the inner portion 308 of the hooks 110 face the bulbous end 104. In particular, when viewed from the top of the device 100 so that the curved portion 304 of a given hook 110 is directly over and covers the axis 402, the inner portion 308 faces the axis 402 so that the curvature of the hook 110 or the curvature of the curved portion 304 is not visible. In the top view of FIG. 2, the top 310 of the curved portion 304 of most of the hooks 110 are visible with respect to the attachment site 312 of the hook 110. At least a majority of fiber hooks 110, preferably all of the hooks 110, are oriented in this way. Thus, the top 310 of curved portions 304 of at least a majority of fiber hooks 110, preferably all of the hooks 110, are oriented parallel to the central axis 402 in FIG. 2. For example, the curved portion 304 in FIGS. 1 and 2 is at 0° in the coordinate system defined in FIG. 4 and employed throughout the present description. However, it should be understood that the curved portion 304 of the hook 110 need not be perfectly aligned to the axis 402 so that the curvature is not visible. For example, in some embodiments, nearly the entire curvature may be visible. In any of these cases, at least a majority of fiber hooks 110, preferably all of the hooks 110, on end portions 104, 106 are, in accordance with exemplary embodiments, concave with respect to an axis 402 of the rod 102.

The configuration of the hooks depicted in FIGS. 1 and 2 enable the fiber hooks 110 to predominantly slide across ear wax attached to an ear canal as the end 104 of the rod 102 is inserted into an ear. In addition, as the end 104 of the rod 102 is removed out of the ear, the fiber hooks predominantly grasp and hold the ear wax, permitting the user holding the rod 102 to pull the ear wax out of the ear. Further, it should be noted that, after the end 104 of the rod 102 is inserted into the ear canal, a user can rotate the rod 102 about the axis 402 and the hooks 112 would similarly slide across the ear wax. However, when the end 104 of the rod 102 is removed from the ear canal, the hooks are configured to grasp and hold the ear wax as discussed above. It should be further noted that the hooks 110 are preferably flexible such that the fiber hooks are compressed toward the rod 102 when the end 104 is inserted into the ear and is in contact with any portion of the ear or the ear wax. The flexibility of the fiber hooks 110 enables the fiber hooks to extend away from the rod when the hooks grasp the ear wax as the end 104 is removed out of the ear.

It should be noted that the top 310 of the curved portion 304 need not be parallel to the central axis 402 in other embodiments. In general, in accordance with exemplary aspects, at least a majority of the fiber hooks 110 can be oriented such that the majority of fiber hooks are concave with respect to a second end of the rod. For example, from the view point of the end 106 of rod 102, at least a majority of fiber hooks 110, preferably all of the hooks 110, on end portion 104 are concave. In FIGS. 1, 2, 4-8, 13 and 14, all of the illustrated hooks 110 are concave with respect to the second end 106 of the rod 102. For example, hooks 110 that are concave with respect to a second end of the rod have tops 310 of the curved portions 304 that are disposed at an angle between −90° and 90° in FIG. 4. In accordance with other exemplary embodiments, at least a majority of the fiber hooks 110 can be oriented such that the majority of fiber hooks are substantially parallel to the central axis 402. In the case in which fiber hooks 110 are substantially parallel to the central axis 402, the tops 310 of the curved portions 304 are disposed at an angle at or between −45° and 45° with respect to the axis 402. For example, FIGS. 5-8 illustrate examples of at least a majority of fiber hooks 110 that are substantially parallel to the central axis 402. Alternatively, in accordance with other exemplary embodiments, at least a majority of the fiber hooks 110 can be oriented such that the majority of fiber hooks are approximately parallel to the central axis 402. In the case in which fiber hooks 110 are approximately parallel to the central axis 402, the tops 310 of the curved portions 304 are disposed at an angle at or between −15° and 15°. For example, FIGS. 2 and 8 illustrate examples of at least a majority of fiber hooks 110 that are parallel to the central axis 402, which is a preferred case (0°) of hooks 110 that are disposed at an angle at or between −15° and 15°. It should also be noted that, in accordance with exemplary embodiments, at least a majority of the fiber hooks 110 can be oriented such that the majority of fiber hooks are perpendicular to the central axis 402. In this particular case, the tops 310 of the curved portions 304 of at least a majority of the hooks 110 are disposed at an angle of −90° and 90° in FIG. 4. Although this case is not preferable and is likely the least effective, at least some of the hooks 110 may nonetheless slide across and grasp ear wax during insertion and extraction as discussed above.

Figure 5:
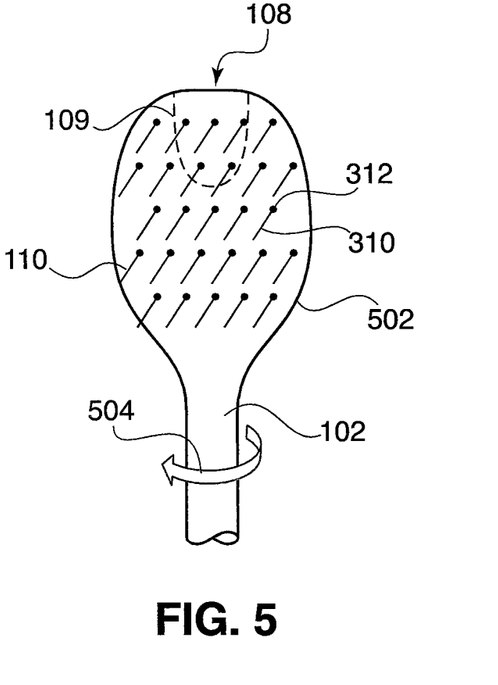
FIG. 5 is a drawing of an end of an ear cleaning device illustrating one example of an orientation of hooks in accordance with an exemplary embodiment of the present application.
Figure 6:
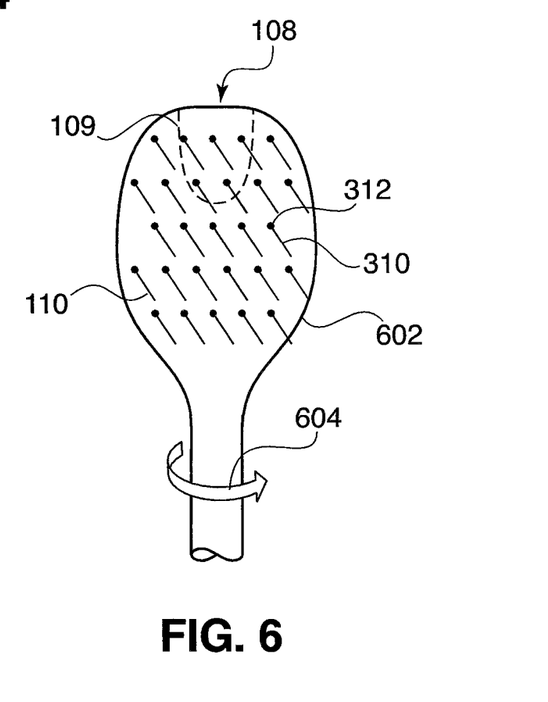
FIG. 6 is a drawing of an end of an ear cleaning device illustrating another example of an orientation of hooks in accordance with an exemplary embodiment of the present application.
Figure 7:
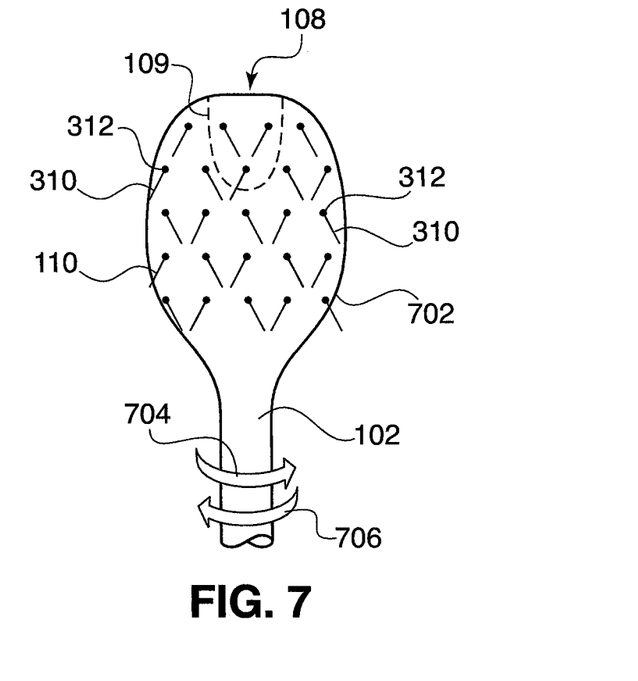
FIG. 7 is a drawing of an end of an ear cleaning device illustrating another example of an orientation of hooks in accordance with an exemplary embodiment of the present application.
Figure 8:
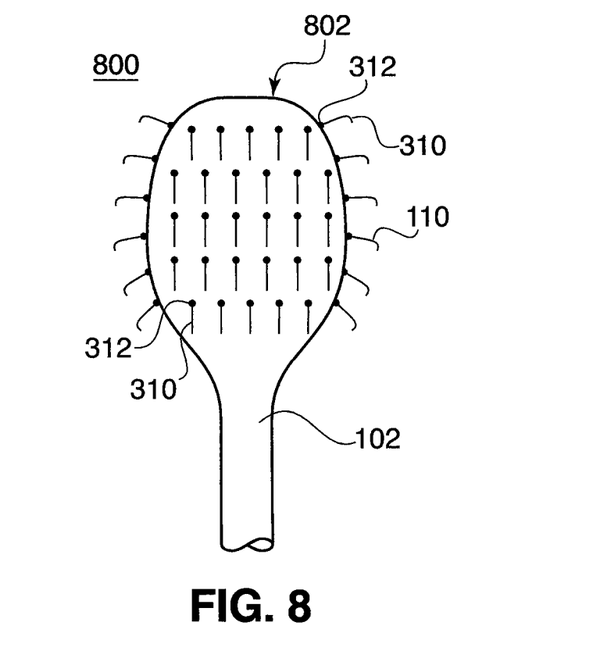
FIG. 8 is a drawing of an end of an ear cleaning device of an exemplary embodiment of the present application illustrating an alternative end portion structure.

Referring to FIGS. 5-7, 13 and 14, with continuing reference to FIGS. 1-4, examples of ends 502, 602, 702, 1302 and 1402 are respectively depicted. Ends 502, 602, 702, 1302 and 1402 can replace any one or both of ends 104 and 106 in FIGS. 1 and 2. Further, it should also be noted that any combination of two ends selected from 102, 104, 502, 602, 702, 1302 and/or 1402 or other end configurations applying the principles described herein, can be employed in various embodiments of an ear cleaning device of the present application. In FIG. 5, at least a majority of the hooks 110 are disposed at a negative angle with respect to the axis 402, and, in this particular embodiment, are disposed at an angle between −45°, and 0° with respect to the axis 402. This configuration can be beneficial in that it may improve gripping of ear wax when the rod 102 is rotated about the axis 402 in a direction 504 after the end 502 is inserted into the ear. In turn, at least a majority of the hooks 110 are disposed at a positive angle with respect to the axis 402 in FIG. 6, and, in this particular embodiment, are disposed at an angle between 0° and 45° with respect to the axis 402. This configuration may improve gripping of ear wax when the rod 102 is rotated about the axis 402 in a direction 604 after the end 602 is inserted into the ear. FIG. 7 illustrates another embodiment in which approximately half of the total number of hooks 110 are oriented at an angle between −45° and 0° with respect to the axis 402 and the other approximate half of the total number of hooks 110 are oriented at an angle between 0° and 45° with respect to the axis 402. This configuration may improve gripping of ear wax when the rod 102 is rotated about the axis 402 in either direction 704/706 after the end 702 is inserted into the ear.

Figure 13:
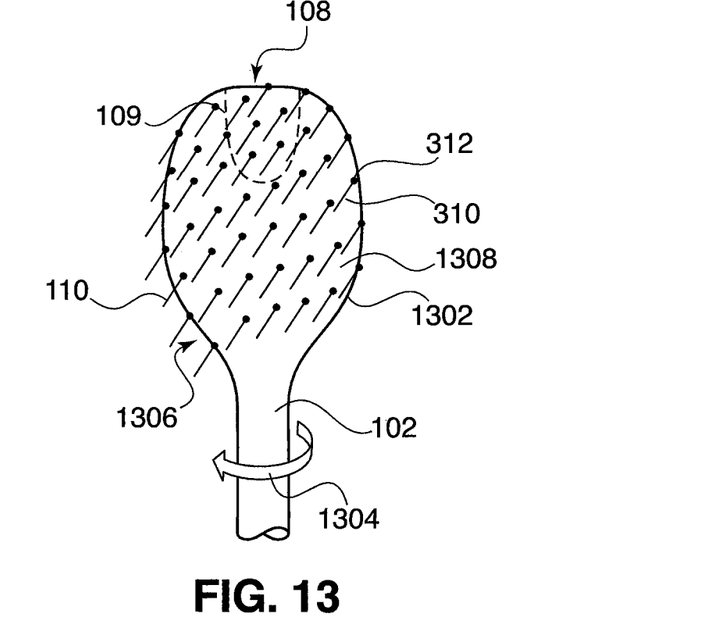
FIG. 13 is a drawing of an end of an ear cleaning device illustrating one example of a configuration of hooks in accordance with an exemplary embodiment of the present application.
Figure 14:
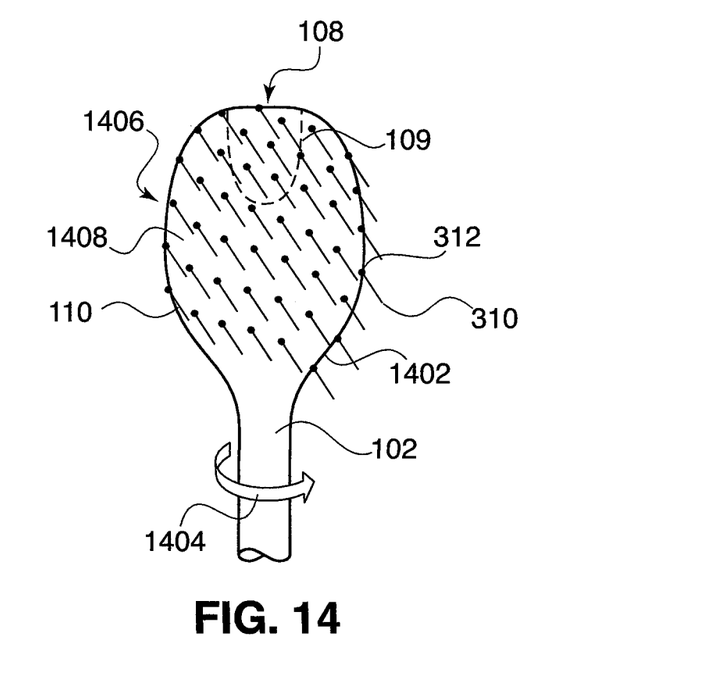
FIG. 14 is a drawing of an end of an ear cleaning device illustrating one example of a configuration of hooks in accordance with another exemplary embodiment of the present application.

Further, FIG. 13 depicts an alternative embodiment of an end portion 1302 in which at least a majority or a portion of the the hooks 110 are configured as a spiral 1306, while FIG. 14 depicts an embodiment of an end portion 1402 in which at least a majority or a portion the hooks 110 are configured as a different spiral 1406. The end portions 1302 and 1402 are essentially the same, except that the spirals 1306 and 1406 run in different directions, as shown in FIGS. 13 and 14, respectively. Here, the spiral 1306/1406 is configured similar to a screw thread, where not only the hooks 110 of the spiral 1306/1406 themselves capture the ear wax, but also the spaces 1308/1408 between different portions of the spiral 1306/1406 trap ear wax as well. In the end 1302, the hooks 110 in the spiral 1306 are oriented at or between 0° and −90° with respect to the axis 402 in FIG. 4, preferably at or between 0° and −45° with respect to the axis 402 and most preferably at −45° with respect to the axis 402. The spiral configuration of spiral 1306 can be beneficial in that it may improve gripping of ear wax by the hooks 110 of the spiral 1306 and/or trapping of ear wax in spaces 1308 when the rod 102 is rotated about the axis 402 in a direction 1304 after the end 1302 is inserted into the ear. Thereafter, the end 1302 can be pulled out of the ear canal to remove the gripped and/or trapped ear wax out of the ear. Similarly, in the end 1402, the hooks 110 in the spiral 1406 are oriented at or between 0° and +90° with respect to the axis 402 in FIG. 4, preferably at or between 0 and +45° with respect to the axis 402 and most preferably at +45° with respect to the axis 402. The spiral configuration of spiral 1406 can also be beneficial in that it may improve gripping of ear wax by the hooks 110 of the spiral 1406 and/or trapping of ear wax in spaces 1408 when the rod 102 is rotated about the axis 402 in a direction 1404 after the end 1402 is inserted into the ear. Thereafter, the end 1402 can be pulled out of the ear canal to remove the gripped and/or trapped ear wax out of the ear.

In accordance with preferred embodiments, the ends of the rod 102 include a respective cavity 108 delineated by cavity wall 109, as illustrated in FIGS. 1, 2, 4-7, 11, 13 and 14. The cavity 108 is configured to, collect any excess ear wax in the ear canal. The cavity 108 is illustrated in a front view, depicted in FIG. 11, of the ear cleaning device 100 of FIG. 1. The cavity 108 is delineated by border 109 and, if, for example, the rod 102 is plastic, can be molded into the plastic of the rod 102. Alternatively or additionally, the cavity 108 can be formed in foam composing the end portion 104/106, and optionally, in the end of the rod 102 on which the foam is deposited. However, it should be understood that the cavity 108 is optional and that other configurations can be employed. For example, FIG. 8 illustrates an example of an end 802 in which no cavity is present and the bulb forming the end 802 of the rod has a contiguous surface. Any one or more of the orientations and configurations of the hooks 110 and rod ends in the embodiments discussed above with respect to FIGS. 1, 2, 4-7, 11, 13 and 14 can omit the cavity 108 and can have a contiguous bulb surface as illustrated in FIG. 8 and in FIG. 12, which is a drawing of a front view of the ear cleaning device 800 of FIG. 8.

Figure 9:
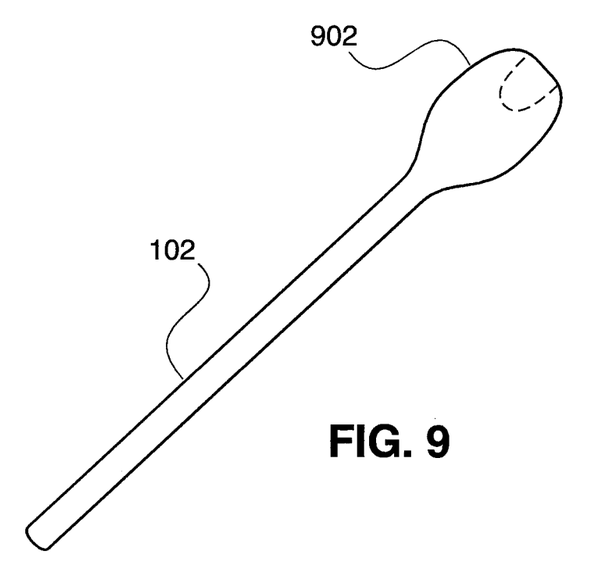
FIG. 9 is a drawing of an ear cleaning device of an exemplary embodiment of the present application illustrating an alternative rod structure.
Figure 10:
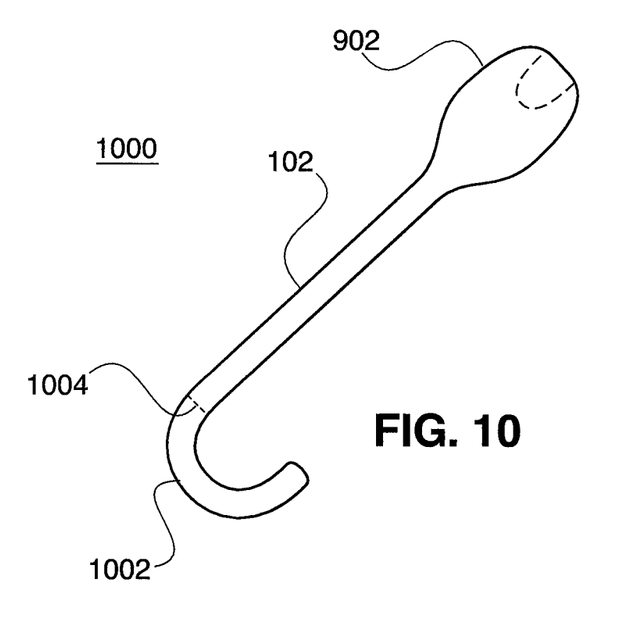
FIG. 10 is a drawing of an ear cleaning device of an exemplary embodiment of the present application illustrating another alternative rod structure.

It should be further understood that ear cleaning devices in accordance with exemplary embodiments need not employ two ends that comprise fiber hooks. For example, as illustrated in FIG. 9, according to an exemplary embodiment, only one end portion 902 including fiber hooks can be utilized. Here, the end portion 902 can be configured as any of the end portions 104, 502, 602, 702. 802, 1302 and 1402 discussed above with respect to FIGS. 1, 2, 5-8, 13 and 14. Moreover, the rod 102 can have a variety of different shapes. For example, as shown in FIG. 10, the ear cleaning device 1000 can include the end portion 902, rod 102 and a hooked handle 1002 that is contiguous with the rod 102. Here, for purposes of assessing the orientation of hooks 110, the fiber hooks 110 are concave with respect to the second end of the rod denoted by 1004, where the second end corresponds to the portion of the device at which the rod shape of the rod 102 ends.

Figure 11:
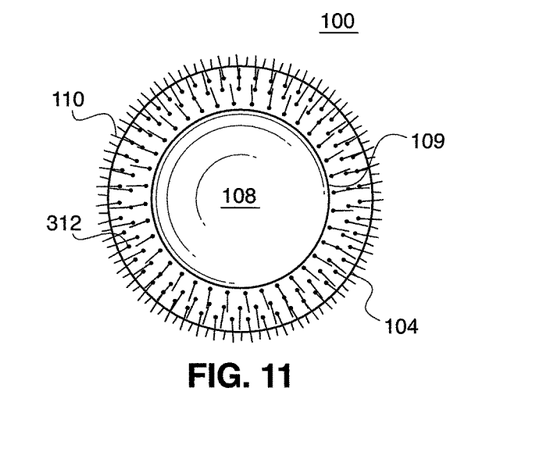
FIG. 11 is a drawing of a front view of an ear cleaning device of an exemplary embodiment of the present application.
Figure 12:
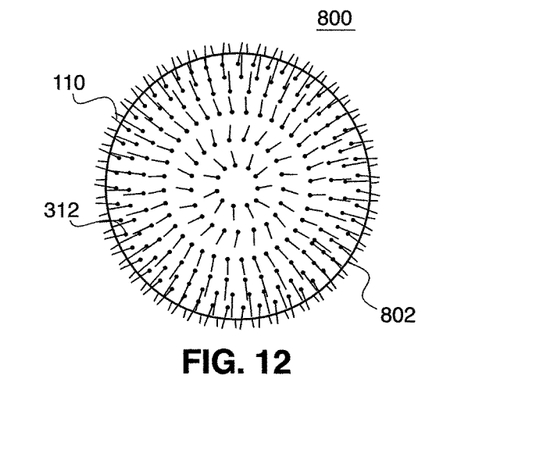
FIG. 12 is a drawing of a front view of an ear cleaning device of an exemplary embodiment of the present application illustrating an alternative end portion structure.

In accordance with each of the embodiments discussed herein above, the fiber hooks 110 can be distributed such that the plurality of hooks enclose the rod. For example, as illustrated in FIGS. 2 and 11, a row of hooks 202 can extend around the circumference of the entire bulb of the end 104, thereby encircling or enclosing the rod 102.

In each of the embodiments described above, the length of the ear cleaning device, referenced as "L" in FIG. 1, can, for example, be at or between 7 cm and 9 cm. Further, in each of the embodiments described above, the diameter of the rod 102, denoted as "D" in FIG. 2, can, for example, be at or between 2 mm and 3 mm. In addition, the end portion and the fiber hooks 110 can be configured such that the top portions 310 of the hooks 110 extend from the axis 402 of the rod to a distance (d), wherein 1 mm≤d≤7 mm, preferably 3 mm≤d≤5 mm, as, for example, referenced in FIG. 2. The length of the hook from the top 310 of the curved portion 304, as indicated in FIG. 3, to the attachment site 312 of the hook 110 is preferably in the range (end points inclusive) of 1/32 inch to 1/4 inch, and is most preferably 1/16 inch. In addition, the length of the hook 110, when straightened, measured from the attachment site 312 to the end 314 of the curved portion 304 is preferably in the range (end points inclusive) 3/32 inch to 5/16 inch, and is most preferably 2/16 inch. However, it should be noted that the curvature of the curved portion 304 can be varied for different lengths within the preferred straightened length range, and within other ranges. In addition, the areal number density of hooks 110 per unit area on the end portion 104/106 can be uniform or can vary along the surface of the end portion 104/106.

Having described exemplary and non-limiting embodiments of an ear cleaning device, it is noted that modifications and variations can be made by persons skilled in the art in light of the description provided above. It is therefore understood that changes and alterations may be made in the embodiments disclosed herein that are within the scope and spirit of the present principles as outlined by the claims provided herein below. Having thus described the present principles with the details and particularity required by the patent laws, what is claimed and desired protected by Letters Patent is set forth in the appended claims.

What is claimed is:

1. An ear cleaning device comprising:
    a rod configured to be held by a user, wherein the rod includes a first end and a second end opposing the first end; and
    a plurality of fiber hooks disposed at the first end of the rod for insertion into the ear such that said fiber hooks are configured to grasp ear wax that is in the ear, and to hold the ear wax when the rod is removed out of the ear,
    wherein, when gravity is the only force acting on at least a majority of fiber hooks disposed at the first end of the rod configured to grasp any ear wax in the ear, said majority of fiber hooks are oriented such that the majority of fiber hooks are concave with respect to the second end of the rod in any orientation of said rod.

2. The ear cleaning device of claim 1, wherein said majority of fiber hooks are oriented such that the majority of fiber hooks are concave with respect to an axis of the rod.

3. The ear cleaning device of claim 1, wherein said majority of fiber hooks are oriented substantially parallel to an axis of the rod.

4. The ear cleaning device of claim 1, wherein the majority of fiber hooks are configured such that the majority of fiber hooks predominantly slide across said ear wax as the first end of the rod is inserted into the ear and predominantly grasp the ear wax as the first end of the rod is removed out of the ear.

5. The ear cleaning device of claim 1, wherein the majority of fiber hooks are flexible such that the majority of fiber hooks are compressed toward the rod when the first end is inserted into the ear and is in contact with any portion of the ear or the ear wax.

6. The ear cleaning device of claim 5, wherein the majority of fiber hooks are flexible such that the majority of fiber hooks extend away from the rod when the hooks grasp the ear wax as first end of the rod is removed out of the ear.

7. The ear cleaning device of claim 1, wherein the plurality of fiber hooks are distributed such that the plurality of hooks enclose the rod.

8. The ear cleaning device of claim 7, wherein the plurality of fiber hooks are distributed about a circumference of the first end.

9. The ear cleaning device of claim 1, wherein the plurality of fiber hooks is a first plurality of fiber hooks and wherein the device comprises a second plurality of fiber hooks disposed at the second end of the rod.

10. The ear cleaning device of claim 1, wherein the device includes a cavity at said first end to collect excess ear wax.

11. The ear cleaning device of claim 1, where a length (L) of the ear cleaning device along an axis of the rod is configured such that $7\ cm \leq L \leq 9\ cm$.

12. The ear cleaning device of claim 1, wherein the plurality of hooks extend from an axis of the rod to a distance (d), wherein $1\ mm \leq d \leq 7\ mm$.

13. The ear cleaning device of claim 1, wherein a diameter (D) of the rod is configured such that $2\ mm \leq D \leq 3\ mm$.

14. The ear cleaning device of claim 1, wherein the plurality of fiber hooks comprise nylon.

15. An ear cleaning device comprising:
    a rod configured to be held by a user, wherein the rod includes a first end and a second end opposing the first end; and
    a plurality of fiber hooks disposed at the first end of the rod for insertion into the ear such that said fiber hooks are configured to grasp ear wax that is in the ear, and to hold the ear wax when the rod is removed out of the ear,
wherein at least a majority of fiber hooks disposed at the first end of the rod configured to grasp any ear wax in the ear are oriented such that the majority of fiber hooks are concave with respect to the second end of the rod, wherein the curvatures of said majority of fiber hooks are greater at ends of the majority of fiber hooks disposed away from the rod than ends of the majority of fiber hooks that attach to the rod.

* * * * *